United States Patent [19]

Seth

[11] Patent Number: 4,844,903
[45] Date of Patent: Jul. 4, 1989

[54] PROCESS FOR THE PRODUCTION OF AN ADHESIVE PLASTER

[75] Inventor: Pawan Seth, Oberwil, Switzerland

[73] Assignee: Mepha AG, Aesch, Switzerland

[21] Appl. No.: 117,554

[22] Filed: Nov. 6, 1987

[30] Foreign Application Priority Data

Nov. 7, 1986 [CH] Switzerland .......................... 4457/86

[51] Int. Cl.$^4$ ............................................. A61F 13/02
[52] U.S. Cl. ................................... 424/448; 421/449; 421/447
[58] Field of Search ................ 424/446, 447, 448, 449

[56] References Cited

U.S. PATENT DOCUMENTS

| | | |
|---|---|---|
| 3,598,122 | 8/1971 | Zaffaroni ............................ 424/435 |
| 3,731,683 | 5/1973 | Zaffaroni ............................ 424/434 |
| 3,742,951 | 7/1973 | Zaffaroni ............................ 424/434 |
| 3,996,934 | 12/1976 | Zaffaroni ............................ 424/484 |
| 4,272,507 | 6/1981 | Figala ................................. 514/447 |
| 4,466,953 | 8/1984 | Keith et al. ........................ 424/449 |
| 4,573,995 | 3/1986 | Chen .................................. 424/449 |
| 4,585,452 | 4/1986 | Sablotsky .......................... 424/449 |
| 4,605,548 | 8/1986 | Ushiyama et al. ................. 424/449 |

FOREIGN PATENT DOCUMENTS

| | | |
|---|---|---|
| 0013606 | 2/1981 | European Pat. Off. . |
| 0033615 | 12/1983 | European Pat. Off. . |
| 2920500 | 11/1980 | Fed. Rep. of Germany . |
| 3119752 | 1/1982 | Fed. Rep. of Germany . |
| 2073588 | 10/1981 | United Kingdom . |

*Primary Examiner*—Thurman K. Page
*Assistant Examiner*—L. R. Horne
*Attorney, Agent, or Firm*—Birch, Stewart, Kolasch & Birch

[57] ABSTRACT

The process results in an adhesive plaster for the transdermal adminstration of pharmaceutical, in particular heat-sensitive, active substances, composed of an adhesive layer, a backing layer, a matrix layer containing the active substances, and a protective layer. The flux of active substance release is controlled by its diffusion from the matrix layer. The latter is produced by the hot melt method, by mixing an ethylene/vinyl acetate copolymer and an involatile, hydrophobic excipient which is miscible with the latter, is compatible with the active substance and is tolerated by the skin, for example isopropyl myristate or a triglyceride, at the melting point of the mixture, and incorporation therein of a solution or dispersion of the active substance in a small amount of the same excipient.

5 Claims, 1 Drawing Sheet

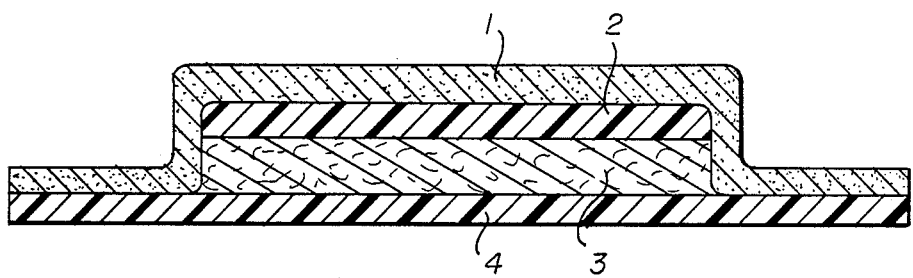

PROCESS FOR THE PRODUCTION OF AN ADHESIVE PLASTER

The invention relates to a process for the production of an adhesive plaster for the transdermal administration of a systemically acting pharmaceutical active substance which can be absorbed through the skin, and to the adhesive plaster produced by the process.

Adhesive plasters meant for the transdermal administration of a systemically acting active substance are also called occlusive dressings. In this connection, a very general distinction is made between three different types based on the principle used to control active substance release, namely: (1) control by means of a semipermeable membrane, or (2) control by diffusion from a matrix containing the active substance, or (3) control by dissolution of microcapsules containing the active substance.

In the process according to the invention, the second type of control of release is used: the active substance is present embedded in a matrix layer and is, on application, released therefrom to the skin in a slow and uniform manner by a diffusion process.

Adhesive plasters of the type described above—that is to say those based on the principle of diffusion from a matrix layer—have, as a rule, hitherto been produced by the coating method. Moreover, this method also represented the only possibility in the case of heat-sensitive active substances (GB patent application No. 2,073,588 A, page 3).

In this method, the active substance is dissolved in an organic solvent, for example an aromatic hydrocarbon such as benzene, or a halogenated hydrocarbon such as chloroform, the solution is applied to a backing layer, and the solvent is evaporated. The application of the solution and the evaporation of the solvent are repeated until the matrix layer has the desired thickness.

It is true in this connection that relatively costly vacuum systems are required for evaporating the solvent. In addition, the organic solvents used (benzene, halogenated hydrocarbons) are not innocuous; for this reason every last trace of them must be removed, and the matrix layer or the adhesive plaster must be subjected to stringent testing for any solvent residues. However, it was necessary to accept these disadvantages and the considerable effort expended because no other method has hitherto been available, at least for heat-sensitive active substances (loc. cit., see above).

Surprisingly, a process has now been found which can be used to produce adhesive plasters for active substances of the type mentioned in the introduction, in particular for heat-sensitive active substances, likewise with control of release by diffusion from a matrix layer, but without using the abovementioned coating method. The matrix layer is produced according to the invention by what is called the hot melt method.

In the latter method the matrix layer containing the active substance is produced by melting together the active substance and an organic polymer, which as a rule requires temperatures of 120° to 190° C. For this reason application of this method to heat-sensitive active substances has hiherto been regarded as entirely ruled out: it would have been necessary in this connection to expect decomposition of the active substance. In general, such high temperatures are avoided where possible, based on a general requirement for caution, in the processing of pharmaceutical active substances. This is probably why the said method has not hitherto entered pharmaceutical technology.

It has now been possible, by the process according to the invention, to overcome the prejudice which exists against the use of the hot melt method for, in particular, heat-sensitive active substances. The process comprises the matrix layer being produced by (1) mixing an ethylene/vinyl acetate copolymer and an involatile excipient which is miscible with the said copolymer, has a mainly or exclusively hydrophobic nature, is inert towards the active substance and is tolerated by the skin, in a ratio of 1 part by weight of copolymer to about 0.3 to 15 parts by weight of excipient, at the melting point of the mixture, until a single homogeneous phase (A) has formed, and (2) mixing the calculated amount of active substance, either as such or in the form of a solution or a homogeneous dispersion (B) in an amount of the said excipient which is less than the amount used in (A), with the phase (A) at its melting point, until a homogeneous composition (C) has formed, and applying the molten composition (C) in the desired layer thickness to an impermeable backing layer, and allowing it to cool and solidify thereon.

Thus, according to the invention, the system obtained as matrix layer is completely hydrophobic in nature and, accordingly, has properties which are completely different from those of the known hydrophilic systems, in particular with regard to the distribution of the active substance between the matrix layer and the skin. The system solidifies at room temperature to a solid composition; the matrix layer is then in the form of a solid, non-aqueous solution or dispersion.

Compared with the coating method, the new process has considerable advantages. The omission of any organic solvent, and the restriction to innocuous auxiliaries, disposes, first of all, of the objections which would necessarily be caused by any solvent residues from the medical viewpoint; this also disposes of the necessity for subsequent testing of the product for solvent residues. Moreover, the costly vacuum systems hitherto used are dispensed with in favor of a very low-cost processing technique. The latter is further simplified to the extent that the application of the matrix layer (including active substance) to the backing layer can be brought about in a single working step.

The invention is described in more detail hereinafter.

The process is generally suitable for pharmaceutical active substances which display a systemic action and are absorbed through the skin. These include active substances having a wide variety of structures and modes of action, such as, for example, the analgesic buprenorphine and its salts, for example buprenorphine hydrochloride, the antihypertensive clonidine, the coronary dilators and calcium antagonists nifedipine and nicardipine, the mydriatic and spasmolytic scopolamine, and the particularly heat-sensitive organic nitrates such as nitroglycerin, erythritol tetranitrate, pentaerythritol trinitrate, mannitol hexanitrate, isosorbide mononitrate, isosorbide dinitrate or trolnitrate.

Of course, nitroglycerin is usually not employed as such, because of its sensitivity to impact or heat, but is employed in the form of a homogeneous mixture with lactose; the mixture advantageously contains, for example, 10% nitroglycerin.

BRIEF DESCRIPTION OF DRAWINGS

Referring to FIGURE, when the adhesive plaster obtained by the process is viewed from the surface which is located on the outside when used on the skin, it comprises (1) a pressure-sensitive adhesive layer on the inner side (that is to say pointing towards the skin), (2) an impermeable backing layer, (3) a matrix layer containing the active substance, and (4) an inert protective layer. The term matrix layer hereinafter is intended to be understood to be the layer which contains the active substance and releases it by slow diffusion.

As a rule, the backing layer (2) and the matrix layer (3) have the same dimensions; in contrast, the adhesive layer (1) projects beyond the edges of the backing layer (and thus also those of the matrix layer) so that the projecting part of its pressure-sensitive inner side lies on the skin when the plaster is used. The protective layer (4) serves to protect the adhesive plaster from any undesired contact, in particular from sticking together of the individual plasters in the package, until it is used; it is removed immediately before use. In general, the adhesive layer (1) and the protective layer (4) have the same dimensions.

The nature of the adhesive layer, of the backing layer and of the protective layer, their arrangement and the details of manufacture require no special explanation because they are already known from the coating method.

The essential components of the matrix layer are, besides the pharmaceutical active substance itself, on the one hand an ethylene/vinyl acetate copolymer, and on the other hand the excipient which has already been mentioned and is miscible with the latter.

The ethylene/vinyl acetate copolymer can contain various contents of vinyl acetate, from about 18 to about 40%; the particular composition is indicated in the examples by the number following (in parentheses) the name of the copolymer. Copolymers having a low vinyl acetate content prove to be more friable in the composition of the matrix layer than do those having a higher vinyl acetate content. On the other hand, the copolymers having a higher vinyl acetate content produce a rather viscous composition when more than 35% by weight of isopropyl myristate are introduced into the composition. Experiments have shown that the physical properties of the ethylene/vinyl acetate (28) copolymer are most suitable for the production of the matrix layer, and that there is excellent transdermal absorption from a corresponding matrix layer.

The hydrophobic excipient which is miscible with the copolymer may be, in particular, isopropyl myristate, a glyceride, a naturally occurring oil or fat, a hydrogenated oil or fat, a fatty acid of medium or higher chain length, a mineral oil or a wax.

The ratio by weight of the ethylene/vinyl acetate copolymer to the excipient, for example isopropyl myristate or a glyceride, in the finished matrix layer may be, for example, from 1:0.7 to 1:1.5. If the active substance used is, for example, nitroglycerin in the form of a 10% adsorbate on lactose, it is possible for the matrix layer to have the following composition by weight:

| ethylene/vinyl acetate (28) | 20 to 45% |
|---|---|
| isopropyl myristate | 20 to 45% |
| nitroglycerin/lactose | 20 to 40% |

It is expedient for the production of the matrix layer to dissolve the active substance in a fraction of the excipient which is miscible with the copolymer, and then to add it in this form to the ethylene/vinyl acetate which has been heated to about 60° C. and softened.

The procedure is advantageously such that, in the first stage of the process, from about 10% by weight of the excipient are used to form phase (A) and, in the second stage of the process, up to about 90% by weight of the excipient are used to form the solution or dispersion (B) or the composition (C).

When an excipient whose melting point is above 37° C. is used, for example a glyceride, it should first be brought to its melting point, or slightly above it, and maintained at this temperature until mixed with the ethylene/vinyl acetate; the active substance is then incorporated in the hot mixture. However, it is also possible to suspend the active substance in a little liquid paraffin and to add this suspension to the mixture of the ethylene/vinyl acetate and the excipient which has been heated to about 45°–50° C.

The resulting composition is applied at a temperature of about 45°–50° C. to the backing layer in a thickness which is calculated on the basis of the amount of active substance which is to be released per unit area and time (for example $cm^2$ and hour). The composition is then allowed to cool and solidify to result in a solid coated body. The coated body is then cut to the desired dimensions, and the cut pieces are provided with the pressure-sensitive adhesive layer on the side of the backing layer, and with the inert protective layer on the side of the matrix layer.

On appropriate calculation and observance of the ratios of amounts, the adhesive plaster produced by the process ensures slow and regularly progressive release of the active substance from the matrix layer to the skin. The chosen ratios are preferably such that the release extends over about 24 hours. In some cases, the amount of active substance present in the matrix layer represents a multiple of the total dose to be administered in 24 hours.

The transdermal absorption of the active substance can be followed and determined quantitatively using a device which has been developed especially for this purpose. The skin on the abdomen of a mouse is depilated and cut out, and the skin section is attached to a glass clyinder in such a way that it covers the cut surface of the cylinder with the epidermis located on the inner side. The adhesive plaster is applied to the epidermis side of the skin section before it is attached to the cylinder. The glass cylinder is then immersed vertically in a vessel containing a physiological saline solution which is maintained at a temperature of 37° C. by a waterbath. The subcutaneous side of the skin section (viewed from the cylinder: the outer side) lies on the surface of the saline solution and is in close contact with it. A circulating pump is used to keep the saline solution in constant motion. Samples are automatically taken from the saline solution at regular intervals of time, and are analyzed for their active substance content. In the case of nitroglycerin, for example, the determination is advantageously carried out by high-pressure liquid chromatography.

Using this device it has been possible to show rules which are of crucial importance for the calculation of the active substance concentration in the matrix layer and of the thickness of the matrix layer.

The adhesive plasters used have the same content of nitroglycerin/lactose but different ratios by weight of ethylene/vinyl acetate and isopropyl myristate. It is clearly evident from Table 1 that the transdermal absorption of the nitroglycerin increases in parallel with the increase in the proportion of isopropyl myristate.

TABLE 1

| Composition of the matrix layer | in % by weight | Nitroglycerin absorbed in 24 hours, in mg |
|---|---|---|
| Ethylene/vinyl acetate (28) | 42 | 2.8 |
| Isopropyl myristate | 28 | |
| Nitroglycerin/lactose | 30 | |
| Ethylene/vinyl acetate (28) | 35 | 4.41 |
| Isopropyl myristate | 35 | |
| Nitroglycerin/lactose | 30 | |
| Ethylene/vinyl acetate (28) | 28 | 6.24 |
| Isopropyl myristate | 42 | |
| Nitroglycerin/lactose | 30 | |

The transdermal absorption can also be influenced in the desired manner by the concentration of active substance in the matrix layer. Using the example of nitroglycerin once again, it is possible to show that the extent of the increase in absorpiton is the same as the increase in the concentration of nitroglycerin in the matrix layer; see Table 2.

TABLE 2

| Composition of the matrix layer | in % by weight | Nitroglycerin absorbed in 24 hours, in mg |
|---|---|---|
| Ethylene/vinyl acetate (28) | 42.5 | 2.16 |
| Isopropyl myristate | 42.5 | |
| Nitroglycerin/lactose | 15.0 | |
| Ethylene/vinyl acetate (28) | 35.0 | 4.41 |
| Isopropyl myristate | 35.0 | |
| Nitroglycerin/lactose | 30.0 | |
| Ethylene/vinyl acetate (28) | 30.0 | 5.71 |
| Isopropyl myristate | 30.0 | |
| Nitroglycerin/lactose | 40.0 | |

| | Examples | | | |
|---|---|---|---|---|
| Example | 1 | 2 | 3 | 4 |
| Ethylene/vinyl acetate (28) | 35% | 40% | 42% | 28% |
| Isopropyl myristate | 35% | 40% | 28% | 42% |
| Nitroglycerin/lactose | 30% | 20% | 30% | 30% |

| Example 5 | | Example 6 | |
|---|---|---|---|
| Ethylene/vinyl acetate (40) | 35% | Ethylene/vinyl acetate (18) | 35% |
| Isopropyl myristate | 35% | Isopropyl myristate | 35% |
| Nitroglycerin/lactose | 30% | Nitroglycerin/lactose | 30% |

The total amount of ethylene/vinyl acetate is introduced into a vessel which can be heated with hot water, and somewhat less than three-quarters of the amount of isopropyl myristate are added. The vessel is heated to about 60° C., stirring slowly (5 to 10 revolutions per minute), and stirring is continued at this temperature until a uniform composition has formed. The calculated amount of the product of adsorption of nitroglycerin on lactose (10:90) is added to and mixed with the remainder of the isopropyl myristate. The calculated amount of the resulting mixture is added to the molten composition of ethylene/vinyl acetate and isoproply myristate, stirring slowly (5 to 10 rpm), and stirring is continued at a temperature of 45° to 50° C. until a uniform composition has formed.

The composition which has formed is applied at a temperature of about 45° C. and in the desired thickness per unit area to the backing layer and is allowed to cool and solidify thereon. The solid coated body is cut into pieces of the desired dimensions, and the cut pieces are applied with their backing layer side to the adhesive layer of Durapore ® No. 15381 (manufactured by 3M Deutschland GmbH, Neuss/Federal Republic of Germany). The dimensions of the area of the adhesive layer are such that its edges project beyond the surface of the cut piece and form around the latter a ring-shaped adhesive layer. The surface of the matrix layer and the surrounding ring-shaped adhesive layer are covered by an inert protective layer.

EXAMPLE 7

| Ethylene/vinyl acetate (28) | 20% |
|---|---|
| Triglyceride, for example Witepsol ® E 76 | 50% |
| Nitroglycerin/lactose | 30% |

Witepsol is a suppository composition based on modified triglycerides of saturated vegetable fatty acids; manufacturer: Dynamit Nobel AG, Troisdorf (Federal Republic of Germany).

The total amount of ethylene/vinyl acetate is introduced into a vessel which can be heated with hot water, and is heated to about 60° C., during which the copolymer softens to a viscous composition. Then, somewhat less than three-quarters of the amount of triglyceride are melted, and are added in this state to the softened copolymer at a temperature of 50° C., stirring slowly (5 to 10 rpm). Stirring is continued at the same temperature until a uniform composition and a single phase have formed. The remainder of the triglyceride is melted and, at the melting point, the calculated amount of the product of adsorption of nitroglycerin on lactose (10:90) is added; the mixture is stirred until a uniform composition has formed. The calculated amount of the latter is then added to the molten composition of ethylene/vinyl acetate and triglyceride, stirring slowly (5 to 10 rpm), and stirring is continued at a temperature of 45° to 50° C. until a uniform composition has formed.

The composition which has formed is applied at a temperature of about 45° C. to the backing layer, and the process is continued as in Exampels 1 to 6.

EXAMPLE 8

| Ethylene/vinyl acetate (28) | 20% |
|---|---|
| Liquid paraffin | 10% |
| Triglyceride, for example Witepsol ® E 76 | 40% |
| Nitroglycerin/lactose | 30% |

The total amount of ethylene/vinyl acetate is introduced into a vessel which can be heated with hot water and is heated to about 60° C., during which the copolymer softens to a viscous composition. The total amount of melted triglyceride is added to the softened copolymer at a temperature of 50° C., stirring slowly (5 to 10 rpm), and stirring is continued at this temperature until a uniform composition and a single phase have formed. The calculated amount of the product of adsorption of nitroglycerin on lactose (10:90) is added to the liquid paraffin, and the mixture is stirred until a uniform composition has formed, which then is added to the molten composition of ethylene/vinyl acetate and triglyceride at a temperature of 45° to 50° C., stirring slowly (5 to 10 rpm), and stirring is continued at this temperature until a uniform composition has formed.

The resulting composition is applied to the backing layer, and the process is completed as in Examples 1 to 6.

I claim:

1. A process for the production of an adhesive plaster for the transdermal administration of a systemically acting, heat-sensitive pharmaceutically active substance which can be absorbed through the skin, which plaster is composed of, in sequence, a pressure-sensitive adhesive layer (a), and impermeable backing layer (b), a matrix layer (c) containing the active substance, and an inert protective layer (d), said matrix layer being produced by:
mixing an ethylene/vinyl acetate copolymer and an involatile hydrophobic excipient, said involatile hydrophobic excipient being miscible with said copolymer, inert toward said active substance and tolerated on the skin of a user, in a ratio of 1 part by weight of said copolymer to about 0.3 to 15 parts by weight of said excipient, at the melting point of the mixture, to form a single molten homogenous phase (A);

adding to said homogenous phase (A) at its melting point said active substance, alone, or in a solution or a homogenous dispersion with said excipient, said excipient being present in an amount which is less than the amount used in (A) to form a homogenous molten composition (C);

applying said molten composition (C) in a desired layered thickness to said impermeable backing layer; and cooling said composition (C) to solidify on said impermeable backing layer.

2. The process as claimed in in claim 1, wherein said pharmaceutically active substance is a member selected from the group consisting of an organic nitrate, buprenorphine or its salts, clonidine, nifedipine, nicardipine and scopolamine.

3. The process as claimed in claim 2, wherein said organic nitrate is a member selected from the group consisting of nitroglycerin, erythritol tetranitrate, pentaerythritol trinitrate, mannitol hexanitrate, isosorbide mononitrate, isosorbide dinitrate and trolnitrate.

4. The process as claimed in claim 1, wherein said hydrophobic excipient which is miscible with the copolymer is a member selected from the group consisting of isopropyl myristate, a glyceride, a naturally occurring oil or fat, a hydrogenated oil or fat, a fatty acid of medium or higher chain length, a mineral oil and a wax.

5. The process as claimed in claim 1, wherein said hydrophobic excipient is present in an amount of 10 to 100% by weight for the formation of said phase (A), and is present in an amount of 90 to 0% by weight for the formation of said solution or dispersion (B) or of said composition (C).

* * * * *